US006508954B1

(12) United States Patent
Elnagar et al.

(10) Patent No.: US 6,508,954 B1
(45) Date of Patent: Jan. 21, 2003

(54) 1,3-DIBROMO-5,5-DIMETHYLHYDANTOIN OF ENHANCED PROPERTIES

(75) Inventors: Hassan Y. Elnagar, Baton Rouge, LA (US); Jonathan N. Howarth, Baton Rouge, LA (US); Bruce C. Peters, Baton Rouge, LA (US); Edgar E. Spielman, Jr., Baton Rouge, LA (US); Dustin H. Thomas, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/484,687

(22) Filed: Jan. 18, 2000

(51) Int. Cl.$^7$ .......................... C02F 5/12; A01N 43/50; B29C 47/00

(52) U.S. Cl. ............... 252/180; 252/187.2; 264/211.11; 510/191; 514/389; 514/398; 514/951; 548/317.1

(58) Field of Search .............................. 252/180, 187.2; 548/317.1; 514/398, 951, 389; 510/191; 264/211.11

(56) References Cited

U.S. PATENT DOCUMENTS

| | | | |
|---|---|---|---|
| 2,130,805 A | 9/1938 | Levine | 210/28 |
| 2,392,505 A | 1/1946 | Rogers | |
| 2,398,598 A | 4/1946 | Rogers | |
| 2,779,764 A | 1/1957 | Paterson | |
| 2,795,556 A | 6/1957 | Quinn | 252/187 |
| 2,868,787 A | 1/1959 | Paterson | |
| 2,920,997 A | 1/1960 | Wolf et al. | |
| 2,971,959 A | 2/1961 | Waugh et al. | |
| 2,971,960 A | 2/1961 | Waugh et al. | |
| 3,121,715 A | 2/1964 | Waugh et al. | |
| 3,147,259 A | 9/1964 | Paterson | |
| 3,345,371 A | 10/1967 | Paterson | |
| 3,626,972 A | 12/1971 | Lorenzen | 137/268 |
| 4,078,099 A | 3/1978 | Mazzola | 427/213 |
| 4,126,717 A | 11/1978 | Mazzola | 427/220 |
| 4,136,052 A | 1/1979 | Mazzola | |
| 4,199,001 A | 4/1980 | Kratz | 137/268 |
| 4,242,216 A | 12/1980 | Daugherty et al. | |
| 4,270,565 A | 6/1981 | King, Sr. | 137/268 |
| 4,293,425 A | 10/1981 | Price | 210/754 |
| 4,327,151 A | 4/1982 | Mazzola | 428/407 |
| 4,331,174 A | 5/1982 | King, Sr. | 137/268 |
| 4,382,799 A * | 5/1983 | Davis et al. | 252/187.2 X |
| 4,427,692 A | 1/1984 | Girard | 424/273 R |
| 4,465,839 A | 8/1984 | Schulte et al. | 548/310 |
| 4,532,330 A | 7/1985 | Cole | 548/311 |
| 4,537,697 A | 8/1985 | Girard | |
| 4,560,766 A | 12/1985 | Girard et al. | 548/311 |

(List continued on next page.)

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0177645 | 4/1986 |
| EP | 0206725 | 12/1986 |
| EP | 0228593 | 7/1987 |
| EP | 0581826 | 9/1995 |
| GB | 1054243 | 1/1967 |
| GB | 1600289 | 10/1981 |
| GB | 2273106 | 6/1994 |
| WO | 8910696 | 11/1989 |
| WO | 8630491 | 10/1996 |
| WO | 9715652 | 5/1997 |
| WO | 9720546 | 6/1997 |
| WO | 9720909 | 6/1997 |
| WO | 9743264 | 11/1997 |
| WO | 9743392 | 11/1997 |
| WO | 0034186 | 6/2000 |

OTHER PUBLICATIONS

Corral et al., "Substitution in the Hydantoin Ring. III. Halogenation", J. Org. Chem., 1963, vol. 28, pp. 1100–1104.
Jolles, "General Methods of Bromination", Bromine and its Compounds, 1966, Ernest Benn, London, p. 365.
Markish et al., "New Aspects on the Preparation of 1,3–Dibromo–5,5–Dimethylhydantoin", Ind. Eng. Chem. Res. 1995, vol. 34, pp. 2125–2127.
Orazi et al., "Halogenacion con 3–Bromo–5,5–Dimetil–Hidantoina", Anales Assoc. Quim. Argentina, 1949, vol. 37, pp. 192–196. (Not translated).
Orazi et al., "Halogenacion Con 1–3–Dibromo–5, 5–Dimetil–Hidantoina", Anales Assoc. Quim. Argentina, 1950, vol. 38, pp. 5–11. (Not translated).
HCAPLUS Abstract of JP 07277912 A2 issued 1995.
HCAPLUS Abstract of JP 08027119 A2 issued 1996.
HCAPLUS Abstract of JP 08239699 A2 issued 1996.
HCAPLUS Abstract of JP 09087684 A2 issued 1997.
HCAPLUS Abstract of JP 09227317 A2 issued 1997.
Chowhan et al., "Hardness Increase Induced by Partial Moisture Loss in Compressed Tablets and Its Effect on In Vitro Dissolution", J. Pharm. Sciences, Oct. 1978, vol. 67, No. 10, pp. 1385–1389.
Krycer et al., "An Evaluation of Tablet Binding Agents Part II. Pressure Binders", Powder Technology, 1983, vol. 34, pp. 53–56.

(List continued on next page.)

Primary Examiner—Richard D. Lovering
(74) Attorney, Agent, or Firm—Edgar E. Spielman, Jr.

(57) ABSTRACT

Among the enhanced properties of the 1,3-dibromo-5,5-dimethylhydantoins described are their larger average particle sizes, their compactibility even though devoid of a binder, their excellent free-flowing and low-dust properties, and their more appealing aesthetic qualities, as compared to previously known 1,3-dibromo-5,5-dimethylhydantoins. These novel 1,3-dibromo-5,5-dimethylhydantoins can be produced, for example, by concurrently feeding (i) an aqueous solution or slurry formed from an inorganic base and 5,5-dimethylhydantoin, and (ii) a brominating agent, in proportions such that each nitrogen atom is substituted by a bromine atom, thereby forming product which precipitates in an aqueous reaction mixture. The pH of the reaction mixture is maintained in the range of about 5.5 to about 8.5.

32 Claims, No Drawings

U.S. PATENT DOCUMENTS

| | | | |
|---|---|---|---|
| 4,571,333 A | 2/1986 | Hsiao et al. | 424/22 |
| 4,597,941 A | 7/1986 | Bottom et al. | 422/37 |
| 4,621,096 A | 11/1986 | Cole | 514/389 |
| 4,654,424 A | 3/1987 | Girard et al. | 548/311 |
| 4,662,387 A | 5/1987 | King, Sr. | 137/268 |
| 4,677,130 A | 6/1987 | Puzig | 514/389 |
| 4,698,165 A | 10/1987 | Theyson | 210/755 |
| 4,713,079 A | 12/1987 | Chun et al. | 8/101 |
| 4,728,453 A | 3/1988 | Choy | |
| 4,745,189 A | 5/1988 | Lee et al. | 544/221 |
| 4,780,197 A | 10/1988 | Schuman | 210/136 |
| 4,803,079 A | 2/1989 | Hsiao et al. | 424/468 |
| 4,867,895 A | 9/1989 | Choy | |
| 4,919,841 A | 4/1990 | Kamel et al. | 252/186.26 |
| 4,925,866 A | 5/1990 | Smith | 514/389 |
| 5,076,315 A | 12/1991 | King | 137/268 |
| 5,137,563 A | 8/1992 | Valkanas | 71/64.07 |
| 5,218,983 A | 6/1993 | King | 137/1 |
| 5,338,461 A | 8/1994 | Jones | 210/755 |
| 5,339,889 A | 8/1994 | Bigham | 165/1 |
| 5,384,102 A | 1/1995 | Ferguson et al. | 422/264 |
| 5,403,813 A | 4/1995 | Lichti et al. | 504/116 |
| 5,409,711 A * | 4/1995 | Mapelli et al. | 514/951 X |
| 5,422,126 A | 6/1995 | Howarth et al. | 424/723 |
| 5,476,116 A | 12/1995 | Price et al. | 137/268 |
| 5,565,109 A | 10/1996 | Sweeny | 210/755 |
| 5,565,576 A | 10/1996 | Hall et al. | 548/317.1 |
| 5,578,559 A | 11/1996 | Dolan et al. | 510/192 |
| 5,591,692 A | 1/1997 | Jones et al. | 504/124 |
| 5,603,941 A | 2/1997 | Farina et al. | 424/405 |
| 5,610,126 A | 3/1997 | Barford et al. | 510/191 |
| 5,614,528 A | 3/1997 | Jones et al. | 514/258 |
| 5,670,451 A | 9/1997 | Jones et al. | 504/134 |
| 5,750,061 A | 5/1998 | Farina et al. | 264/117 |
| 5,753,602 A | 5/1998 | Hung et al. | 510/192 |
| 5,756,440 A | 5/1998 | Watanabe et al. | 510/191 |
| 5,763,376 A | 6/1998 | Ward et al. | 510/191 |
| 5,780,641 A | 7/1998 | Yerushalmi et al. | 548/320.5 |
| 5,859,060 A | 1/1999 | Platt | 514/569 |
| 5,942,153 A | 8/1999 | Heydel | 252/187.33 |
| 5,958,853 A | 9/1999 | Watanabe | 510/192 |
| 5,972,864 A | 10/1999 | Counts | 510/192 |
| 5,981,461 A | 11/1999 | Counts et al. | 510/365 |
| 5,984,994 A | 11/1999 | Hudson | 71/28 |

OTHER PUBLICATIONS

Petterson, "N-Halogen Compounds. I. Decomposition of 1,3-Dichloro-5,5-dimethylhydantoin in Water at pH 9", J. Org. Chem., 1959, vol. 24, pp. 1414–1419.

March, "Advanced Organic Chem.", 1992, 4$^{th}$ Edition, pp. 639–640.

HCAPLUS Abstract of JP 07171576 A2 issued 1995.

Author unknown, "Big Brother Brominator—Brominators", Bulky Systems Website, <http://www.bulkysystemsinc.com/brominator.html> (Visited Aug. 10, 2001). 1 page.

Author unknown, "Bio Lab Brominator", Conely Company Website, <http://www.conelyco.com/Pool-Spa/parts/biobrom.htm> (Visited Aug. 10, 2001) 2 pages.

Hayward America's #1 Pool Water Systems Product Catalog, "Automatic Chemical Feeders" Chlorinators (Slow Dissolve Tri-Chlor Only) and Brominators, Hayward Pool Products Inc. Website, <http://www.haywardnet.com/products/catalog/displayProdInfo.cfm?itemID=61>, 2 pages.

Hayward Pool Products Owner's Guide, Installation and Operating Instructions, "Hayward Chemical Feeder", Models C250CF, C500CF, C1100CF, C1800CF, C2400CF,—1998—4 pages.

Hayward America's #1 Pool Water Systems Product Catalog, "Automatic Chemical Feeders" Chlorinators (Slow Dissolve Tri-Chlor Only) and Brominators, Buyers Guide, Hayward Pool Products Inc., Website, <http://www.haywardnet.com/products/catalog/displayProdInfo.cfm?itemID=60>, 2 pg.

Pentair Pool Products Brochure, "Rainbow High Capacity Chlorine/Bromine Feeders", "Unsurpassed Performance From The Industry's Leader in Automatic Sanitizing of Large Residential and Commercial Pools", date unknown, 1 page.

Pentair Pool Products Brochure, "Rainbow Model 300 Automatic Chlorine/Bromine Off–line Feeders", "The Efficient, Easy Way to Sanitize Your Pool or Spa", date unknown, 1 page.

Pentair Pool Products Brochure, "Rainbow Model 320 Automatic Chlorine/Bromine In-line Feeder", "Saves Time, Reduces Manual Handling of Chemicals", date unknown, 7 pages.

Sani–King Perform–Max Pool Sanitizer Instruction Guide, Models 910, 940, & 980 (Inline) and Models 930 & 960 (Off–line), date unknown, 16 pages.

Sani–King Spa Feeder Product Brochure Model 740 from King Technology Website, <http://www.kingtechnology.com/spafeeder.htm> Visited (Aug. 10, 2001), 2000, 4 pages.

Sani–King Adjust–A–Flo Product Brochure from King Technology Website <http://www.kingtechnology.com/spafeeder.htm> (Visited Aug. 10, 2001), 2000, 1 page.

Sani–King Perform–Max Sanitizers for Inground Pools Product Brochure for Model 940 & 960 from King Technology Website, <http://www.kingtechnology.com/perfermaxIG.htm>, visited Aug. 10, 2001, 2000, 1 page.

Sani–King Perform–Max Sanitizers for Above Ground Pools Product Brochure Model 910 & 930 from King Technology Website, <http://www.kingtechnology.com/perfermaxIG.htm>, visited Aug. 10, 2001, 2000, 1 page.

Discount Pool & Spa Supplies, Automatic Chlorinators and Chemical Feeders Website, <http://www.discountpoolsupplies.com/Chemfeeders/>, Visited Aug. 10, 2001, 3 pages.

Al–Zahrani, S.M.; "Utilization of Polyethylene and Paraffin Waxes as Controlled Delivery Systems for Different Fertilizers", Ind. Eng. Chem. Res., 2000; vol. 39; pp. 369–371.

* cited by examiner

1,3-DIBROMO-5,5-DIMETHYLHYDANTOIN OF ENHANCED PROPERTIES

REFERENCE TO OTHER APPLICATIONS

Commonly-owned copending application Ser. No. 09/484,844, filed Jan. 18,2000, by some of us, describes and claims chemical processes from which, inter alia, the compositions of the present invention can be formed or derived. Commonly-owned copending application Ser. No. 09/487,816 filed Jan. 18, 2000, by two of us, relates in part to converting 1,3-dihalo-5,5-dimethylhydantoins into compacted articles using novel binders. Commonly-owned copending application Ser. No. 09/484,938, filed Jan. 18, 2000, by one of us and some of our colleagues, describes and claims methods for effecting efficacious microbiological control utilizing 1,3-dibromo-5,5-dimethylhydantoin in novel compacted or non-compacted forms. Commonly-owned copending application Ser. No. 09/484,891, filed Jan. 18, 2000, by one of us, relates to the compacting of 1,3-dihalo-5,5-dimethylhydantoins other than 1,3-dibromo-5,5-dimethylhydantoin without use of binders, and to the novel compacted forms so produced. Commonly-owned copending application Ser. No. 09/183,896, filed Jan. 18,2000, by two of us relates to the granulation of small average particle size 1,3-dibromo-5,5-dimethylhydantoin and also to the compaction of such granulated products to form larger-sized articles.

TECHNICAL FIELD

This invention relates to novel forms of 1,3-dibromo-5,5-dimethylhydantoin which, by virtue of their characteristics and physical properties, are superlative biocidal water-treating agents and brominating agents.

GLOSSARY

As used herein the terms "halogen", "halogenated", and "halo" are with reference to bromine or chlorine, or both.

BACKGROUND 1,3-Dihalo-5,5-dialkylhydantoins, especially 1,3-dibromo-5,5-dimethylhydantoin, 1,3-dichloro-5,5-dimethylhydantoin, 1-bromo-3-chloro-5,5-dimethylhydantoin, and 1-chloro-3-bromo-5,5-dimethylhydantoin, or mixtures of two or more of them, are biocidal agents for use in water treatment. These compounds are, in general, sparingly soluble in water. Each of these compounds except 1,3-dibromo-5,5-dimethylhydantoin, has been supplied in compacted solid forms such as granules, tablets, or briquettes, and delivered into the water being treated by means of water flow through an erosion feeder. The compacted forms of the 1,3-dichloro-5,5-dimethylhydantoin have been produced using a binder. Of the three manufacturers of compacted forms of N,N'-bromochloro-5,5-dimethylhydantoin, two such manufacturers are known to utilize a binder in producing the compacted forms. The technology used by the other manufacturer to produce such compacted forms has not been disclosed. So far as is known, never before has 1,3-dibromo-5,5-dimethylhydantoin powder been converted into a compacted form by any method.

Over the years considerable effort has been devoted to the search for improved methods for producing such compounds. In U.S. Pat. No. 2,971,960 N-brominated compounds such as N-brominated 5,5-di-lower-alkyl hydantoins are formed by treating the alkylhydantoin with bromine in an acidic aqueous solution containing hypochlorite, preferably at a pH between 1 and 4. However, the method of choice has been halogenation of the alkylhydantoin in a basic aqueous medium. Almost invariably the halogen has been introduced into, or formed in situ in, the aqueous medium containing the alkylhydantoin. See in this connection U.S. Pat. Nos. 2,398,598; 2,779,764; 2,868,787; 2,920, 997; 2,971,959; 3,121,715; 3,147,259; 4,532,330; 4,560, 766; 4,654,424; 4,677,130; 4,745,189; PCT Publication No. WO 97/43264, published Nov. 20, 1997; Orazi and Meseri, *Anales Assoc. Quim. Argentina,* 1949, 37, 192–196; Orazi and Meseri, *Anales Assoc. Quim. Argentina,* 1950, 38, 5–11; Corral and Orazi, *J. Org. Chem.,* 1963, 23, 1100–1104; Jolles, *Bromine and its Compounds,* Ernest Benn, London, 1966, p. 365; and Markish and Arrad, *Ind. Eng. Chem. Res.,* 1995, 34, 2125–2127.

The N,N'-dihalogenated dialkylhydantoin products formed by such processes are formed as powdery solids. For use in many applications the dry powders need to be converted into larger forms such as granules, tablets, or briquettes. This in turn has presented problems associated with providing densified or compacted products with sufficient strength to withstand the physical stresses encountered in packaging, conveying, handling, shipping, storage, and use. The nature of these problems have been described, for example, in U.S. Pat Nos. 4,532,330; 4,560,766; 4,654,424; 4,677,130; 4,745, 189; and 5,565,576. The approaches described in these patents for alleviating one or more such problems involve use of additional or other materials. Thus in U.S. Pat. Nos. 4,532,330 and 4,621,096, halogenated dimethylhydantoins are mixed with calcium chloride and water, and the mixture is compacted by compression into the desired shape. In U.S. Pat. Nos. 4,560,766 and 4,654,424, halogenated ethylhydantoins are used instead of halogenated dimethylhydantoins and are compacted as such, or are melt blended with halogenated dimethylhydantoins. U.S. Pat. No. 4,677,130 describes forming dry blends of the halogenated dimethylhydantoin with particulate alkali metal or alkaline earth metal salt followed by compression to form a compacted product such as a tablet. PCT Publication No. WO 97/43264 describes the use of 1,3-bromochloro-5-methyl-5-propylhydantoin as a binder in making compacted forms of halogenated hydantoins.

U.S. Pat. No. 4,745,189 describes formation of halogenated dimethylhydantoin by halogenating the hydantoin in an aqueous mixture under alkaline conditions in the presence of a halogenated alicyclic organic compound such as dichloromethane. The Examples of the patent describe the formation of N,N'-bromochloro-5,5-dimethylhydantoin products comprised of large particles. However, so far as is known, no 1,3-dibromo-5,5-dimethyl-hydantoin having an average particle size of at least 175 microns has been described anywhere in the prior art.

U.S. Pat. No. 4,560,766 teaches that halogenated dimethylhydantoin per se cannot be used for making low-dust powders, granules, tablets, flakes, compacted forms, cast forms, and carrier-coated products without the aid of a binder.

Despite extensive research efforts in the field, a number of additional serious problems remain unsolved. For one thing, processes utilized in the production of 1,3-dihalo-5,5-dimethylhydantoins form powders which have the undesirable characteristic of producing large quantities of irritating, corrosive dusts when handled and used. Further, products formed from bromine-containing 1,3-dihalo-5,5-dimethylhydantoin, which are widely distributed as consumer products, have aesthetic properties that are less than desirable. Typically, products produced from such bromine-containing 1,3-dihalo-5,5-dimethylhydantoins have a distinct yellow coloration.

Other remaining unsolved problems relating to previously known 1,3-dihalo-5,5-dimethylhydantoins involve their lack of acceptable flowability characteristics. In particular, 1,3-dihalo-5,5-dimethylhydantoin powders exhibit high interparticulate friction and thus cannot be readily discharged from feed hoppers or be transferred without "bridging" or "arching" when passing through conduits or screw conveyors. In such operations, "bridging" or "arching" (which are synonymous terms) is a condition in which the particles stick together without fusing to form lumps or clumps or balls of particulate material, which in turn seriously interfere with or impede further flow of the material. Another problem associated with 1,3-dihalo-5,5-dimethylhydantoin powders is their strong tendency to undergo "ratholing" when being discharged from a conical hopper or feeder. This means that, rather than discharging evenly from the device, the powder discharges from the center only, leaving an annular mass of the powder suspended against the interior sloping conical sides of the device. In severe cases, it becomes necessary to release such suspended powder by striking the exterior of the device with a hammer or baseball bat.

It would be of considerable advantage if 1,3-dibromo-5,5-dimethylhydantoins could be provided as powders having little or no dusting characteristics. It would also be of great advantage to provide particulate 1,3-dibromo-5,5-dimethylhydantoins useful for making granules, caplets, tablets, flakes, compacted forms, cast forms, and carrier-coated products without the aid of a binder, and without use in the production process of any organic halogen compound such as dichloromethane. Moreover, the provision of 1,3-dibromo-5,5-dimethylhydantoins having an average particle size larger than available heretofore would be a most welcome contribution to the art. Still other features of considerable advantage in the art would be the provision of 1,3-dibromo-5,5-dimethylhydantoins having superior flowability characteristics and more appealing aesthetic properties.

SUMMARY OF THE INVENTION

This invention involves the discovery, inter alia, of 1,3-dibromo-5,5-dimethylhydantoin particulate solids having unique physical properties. Such 1,3-dibromo-5,5-dimethylhydantoin particulate solids can be produced by the process described in commonly-owned U.S. application Ser. No. 09/484,844, filed Jan. 18, 2000.

More particularly, this invention provides 1,3-dibromo-5,5-dimethylhydantoin particulate solids having larger average particle sizes than have been available heretofore in the marketplace. It has been discovered that the 1,3-dibromo-5,5-dimethylhydantoin particulate solids of this invention are ideally suited for compaction and tableting in as much as these operations can be conducted without need of a binder of any kind. Moreover, the 1,3-dibromo-5,5-dimethylhydantoin particulate solids of this invention have little or no dusting characteristics, have superior flowability properties, and possess more appealing aesthetic qualities than commercially-available products of this type.

Accordingly, this invention provides, inter alia, novel 1,3-dibromo-5,5-dimethylhydantoin particulate solids having large average particle sizes, shape-retentive pressure compacted articles produced from binder-free 1,3-dibromo-5,5-dimethylhydantoin particulate solids, and methods of producing such shape-retentive compacted articles from such binder-free 1,3-dibromo-5,5-dimethylhydantoin particulate solids.

One of the unprecedented properties of the 1,3-dibromo-5,5-dimethylhydantoin particulate solids of this invention is their large average particle size. Unlike prior forms of 1,3-dibromo-5,5-dimethylhydantoin which, when obtained from a supplier of laboratory-sized quantities of chemicals for laboratory usage had an average particle size of about 162 microns, and from two large scale producers, had respective average particle sizes of about 45 and about 65 microns, the 1,3-dibromo-5,5-dimethylhydantoin particulate solids of this invention have average particle sizes of at least about 175 microns, and preferably at least about 200 microns. In fact, 1,3-dibromo-5,5-dimethylhydantoin can now be provided having an average particle size of over 500 microns. A highly desirable manifestation of the large average particle sizes of the 1,3-dibromo-5,5-dimethylhydantoin particulate solids of this invention is their freedom from the undesirable characteristic of producing large quantities of irritating, corrosive dusts when handled and used. In operations performed to date, the quantities of dust produced during processing have been remarkably low.

Another of the unprecedented properties of the 1,3-dibromo-5,5-dimethylhydantoin particulate solids of this invention is their compactibility. Not only can they be compacted without use of a binder, but in addition, the compacted forms, even though devoid of a binder, are shape retentive, and in addition have remarkable crush strength. In fact, this invention involves the further discovery that prior 1,3-dibromo-5,5-dimethylhydantoin powders cannot be removed from a tableting die without breakage. In sharp contrast, the pressure compacted larger average particle size 1,3-dibromo-5,5-dimethylhydantoin of this invention can be removed from the die without any breakage occurring. In particular, prior smaller average particle size 1,3-dibromo-5,5-dimethylhydantoin, when released or extracted from a tableting die, "delaminate", meaning that the compacted agglomerate breaks apart into smaller pieces, whereas the 1,3-dibromo-5,5-dimethylhydantoin particulate solids of this invention can be directly converted into shape-retentive tablets of acceptably high physical integrity, without any prior treatment to impart compactibility to the solids.

Moreover, when pressure compacted into granules, tablets, briquettes, or other relatively small shapes, the 1,3-dibromo-5,5-dimethylhydantoin particulate solids of this invention have excellent physical properties for use in water-treatment systems. The shapes erode at slow, but essentially constant, rates when maintained in a constant flow of water. They withstand the customary physical stresses encountered- in packaging, conveying, handling, shipping, storage, and use. The compacted solid forms of this invention produced directly from the larger particle sized 1,3-dibromo-5,5-dimethylhydantoin particulate solids have excellent crush strength even when formed without a binder. In fact, such solid forms when produced with suitable binders have even greater crush strength, and can be converted into even larger non-friable shaped articles such as toilet bowl and swimming pool pucks.

Still another unprecedented property of the 1,3-dibromo-5,5-dimethylhydantoin particulate solids of this invention is their excellent flowability characteristics. In particular, the 1,3-dibromo-5,5-dimethylhydantoin particulate solids of this invention exhibit low interparticulate friction and thus can be readily discharged from feed hoppers, and in addition such particulate solids can be transferred without "bridging" or "arching" when passing through conduits or screw conveyors. In such operations, few, if any, lumps or clumps or balls of particulate material are formed, and thus, little or no interruption of product flow is experienced. Further, in hopper discharging operations, little or no "ratholing" occurs.

Yet another exceedingly desirable property of the 1,3-dibromo-5,5-dimethylhydantoin particulate solids of this invention is their unprecedented creamy white almost white appearance. For example, this invention makes possible the provision of 1,3-dibromo-5,5-dimethylhydantoin particulate solids having a Yellowness Index of about 15 or less. This compound previously available in the marketplace has a distinct yellow coloration which is aesthetically less desirable.

At present the only known way of preparing the novel and eminently useful 1,3-dibromo-5,5-dimethylhydantoin particulate solids of this invention involves use of the process technology described in commonly-owned co-pending application No. 09/484,844, filed Jan. 18, 2000. If in the future other methods can be discovered that produce 1,3-dibromo-5,5-dimethylhydantoin particulate solids having one or more of the unique characteristics of the present invention, such 1,3-dibromo-5,5-dimethylhydantoin particulate solids will of course fall within the scope of the present invention as set forth in the appended claims.

In converting the 1,3-dibromo-5,5-dimethylhydantoin particulate solids of this invention into granules, conventional processing equipment can be used under the usual operating conditions. Typically, 1,3-dibromo-5,5-dimethylhydantoin particulate solids of this invention, with or without a binder, are compressed into sheet form by means of a roll compactor. This sheet in turn is broken up into small granules by a mechanical device, such as a Chilsonator® breaker (The Fitzpatrick Company, Elmhurst, Ill.). The granules are then classified by screening into the desired size range. Undersized granules are typically recycled to the roll compactor, whereas oversized granules are recycled to the breaker device.

Highly suitable apparatus for producing granulated 1,3-dibromo-5,5-dimethylhydantoin is the proprietary MS-75 compactor system (Hosokawa Bepex, Minneapolis, Minn.).

The formation of tablets and other compressed shapes such as briquettes from the 1,3-dibromo-5,5-dimethylhydantoin particulate solids of this invention can utilize known processing equipment and, for the most part, known procedures. However, in conducting compaction of the 1,3-dibromohydantoin particulate solids of this invention in the absence of a binder, it is important that the compaction pressure be sufficient to induce plastic deformation and interparticulate binding of the particles. At the same time, the compaction pressure should not be so great as to produce a compacted product which delaminates on expulsion from the die. Typically, suitable compaction pressures in the practice of this invention will fall within the range of about 1000 to about 30,000 psi, and preferably in the range of about 5000 to about 25,000 psi. Such compaction can be conducted using, for example, a rotary tableting press operated at conventional rotational speeds, e.g., about 20 rpm. Another method for accomplishing the compaction is by means of pressure extrusion through a die orifice, while concurrently shearing the extrudate to produce compacted shapes of the desired size. In such operations, the compaction pressures within the die should be sufficient to induce plastic deformation and interparticulate binding of the particles, but insufficient to produce a compacted product which, when extruded, undergoes an elastic recovery of a magnitude that causes delamination of the compacted extrudate.

In operations conducted on a small scale using manually filled dies, 1,3-dibromo-5,5-dimethylhydantoin particulate solids of this invention having an average particle size of greater than about 175 microns have been successfully compacted into tablets without employment of any binder. The tablets when released from the dies were intact and exhibited no visual surface imperfections.

The 1,3-dibromo-5,5-dimethylhydantoin particulate solids of this invention can also be directly converted without use of a binder into whole briquettes utilizing conventional briquetting rolls operated under conventional conditions. In such operations, pressures in the range of about 1000 to about 30,000 psi are typical; more preferably, the pressures are in the range of from about 5000 to about 25,000 psi. As in the case of pressure compaction of tablets, the compaction pressure should be sufficient to induce plastic deformation and interparticulate binding of the particles, but insufficient to produce a compacted product which undergoes an elastic recovery of a magnitude causing delamination of the compacted article on exiting the rolls.

The compaction operations, whether performed in a die, by extrusion through an orifice of a die, or by roll compaction is typically conducted at ambient room temperatures. However, it is possible to either cool or warm the material being subjected to compaction. This can be accomplished either by refrigerating or directly heating the product before introducing it into the compaction apparatus, or by chilling or heating the apparatus itself such as, for example, by using rolls equipped with heating or cooling coils or other means for effecting temperature regulation. The compaction operation itself can, and in many cases does, result in generation of heat within the compacted shape. Generally speaking, the compaction operations pursuant to this invention can be performed at temperatures in the range of about 5 to about 80° C.

It will be understood and appreciated that departures from the numerical ranges given herein for pressures and temperatures are permissible in the practice of this invention, whenever such departures are deemed necessary or desirable, provided only that such departures do not materially affect in an adverse manner the processing or the properties of the product being produced.

Typically, compacted products of this invention other than granules, e.g., tablets, briquettes, and pucks, formed without use of a binder, will have a crush strength in the range of from about 25 to about 75 pounds per inch of thickness when measured as described hereinafter. Thus, this invention provides tablets which have crush strengths, when measured in the diametral direction (i.e., when a disc-shaped tablet stands on its edge), of from about 25 to about 75 pounds per inch of thickness. In the case of briquettes or other non-disc-shaped articles including granules, the crush strength should be measured in the longitudinal direction, (i.e., with the article standing such that its longest dimension is in the vertical position). Thus, for example, briquettes of this invention have a crush strength of from about 25 to about 75 pounds per inch of thickness when measured in this manner. Granules of this invention will typically have somewhat lower crush strength which, nevertheless, is sufficient for most applications in which granules are to be used. Thus, it is now possible to provide, for the first time, binder-free compacted products having the strength needed to withstand the physical stresses encountered in packaging, conveying, handling, shipping, storage, and use.

When converted into tablets, briquettes, pucks, and other compacted shapes with use of a suitable binder, the 1,3- dibromo-5,5-dimethylhydantoin particulate solids of this invention result in compacted forms of even greater crush strength. Binders suitable for such use include the normally solid, fatty amides such as N,N'-ethylenebisstearamide and related compounds described in U.S. Pat. No. 5,565,576. Markedly superior binding agents for use with the 1,3-dibromo-5,5-dimethylhydantoin particulate solids of this invention are the micronized polyolefin waxes and the micronized polyfluorocarbon waxes described in commonly-owned co-pending application Ser. No. 09/487,816, filed Jan. 18, 2000.

By use of suitable binders, compacted products with crush strengths in the range of from about 60 to about 200 pounds per inch of thickness can be formed. Thus, these compacted products are capable of withstanding, to a greater extent, the physical stresses encountered in packaging, conveying, handling, shipping, storage, and use.

Granules, tablets, and briquettes produced from 1,3-dibromo-5,5-dimethylhydantoin particulate solids of this invention are of particular utility as biocidal agents for use in swimming pools spas, toilet bowl cleaners, cooling towers, air washer systems, wastewater, pulp and paper processing operations, oil field applications, and decorative fountains. Procedures utilizing 1,3-dibromo-5,5-dimethylhydantoin as a biocide and sanitizer in the treatment of aqueous systems or water and its use as an agent to eradicate or reduce biofilm on surfaces contacted with aqueous media are more fully described in commonly-owned copending application Ser. No. 09/484,938, filed Jan. 18, 2000.

As indicated above, one of the unique characteristics of the 1,3-dibromo-5,5-dimethylhydantoin particulate solids of this invention is their unprecedented larger average particle size. So far as is known, 1,3-dibromo-5,5-dimethylhydantoin particulate solids with an average particle size of at least about 175 microns has never before been available, and such particulate solids having at least such average particle size constitute embodiments of this invention. Preferred 1,3-dibromo-5,5-dimethylhydantoin particulate solids of this invention have an average particle size of at least about 200 microns, more preferably at least about 300 microns, still more preferably at least about 400 microns, with 1,3-dibromo-5,5-dimethylhydantoin particulate solids having an average particle size of at least about 500 microns being particularly preferred. Even more preferred are the 1,3-dibromo-5,5-dimethylhydantoin particulate solids of this invention having an average particle size of about 600 microns or more. In each case, the foregoing particle sizes are expressed in terms of 1,3-dibromo-5,5-dimethylhydantoin particulate solids which have not been pressure compacted, nor heat fused, nor agglomerated by means of an organic solvent, nor by means of any other post treatment for particle size enlargement.

In addition, the novel particle size distributions of the 1,3-dibromo-5,5-dimethylhydantoin particulate solids of this invention may contribute materially to the efficacy with which such particulate solids can be compacted.

Thus, in a preferred group of 1,3-dibromo-5,5-dimethylhydantoin particulate solids of this invention in which the average particle size is in the range of at least about 175 microns but less than 300 microns, 50% by weight of the particles have a particle size of at least about 180 microns.

In a particularly preferred group of 1,3-dibromo-5,5-dimethylhydantoin particulate solids of this invention in which the average particle size is in the range of at least about 175 but less than 300 microns, 10 percent by weight of the particles have a particle size of at least about 280 microns, 25 percent by weight of the particles have a particle size of at least about 240 microns, 50 percent by weight of the particles have a particle size of at least about 180 microns, 75 percent by weight of the particles have a particle size of at least about 100 microns, and 90 percent by weight of the particles have a particle size of at least about 45 microns. It is perhaps worth noting that the foregoing weight percentages typically correspond also to volume percentages.

Thus, in a preferred group of 1,3-dibromo-5,5-dimethylhydantoin particulate solids of this invention in which the average particle size is in the range of 300 to about 700 microns, 50% by weight of the particles have a particle size of at least about 350 microns.

In a particularly preferred group of 1,3-dibromo-5,5-dimethylhydantoin particulate solids of this invention in which the average particle size is in the range of 300 to about 700 microns, 10 percent by weight of the particles have a particle size of at least about 500 microns, 25 percent by weight of the particles have a particle size of at least about 440 microns, 50 percent by weight of the particles have a particle size of at least about 350 microns, 75 percent by weight of the particles have a particle size of at least about 120 microns, and 90 percent by weight of the particles have a particle size of at least about 50 microns.

As also described above, this invention provides products in which one or more of the 1,3-dibromo-5,5-dimethylhydantoin particulate solids of this invention are converted into granules, tablets, briquettes, pucks, or any other larger sized product, however produced. Typical operations of this type have been described above. Other procedures include, for example, mixing the 1,3-dibromo-5,5-dimethylhydantoin particulate solids of this invention with other dialkylhydantoins and if desired, heat fusing the resultant mixtures, such as described in U.S. Pat. Nos. 4,560,766 and 4,654,424. Similarly, the 1,3-dibromo-5,5-dimethylhydantoin particulate solids of this invention can be utilized in combination with 1,3-bromochloro-5-methyl-5-propylhydantoin as a binder as described in published PCT Application WO 97/43264.

While there are no hard and fast rules governing differentiation with respect to size among granules, tablets, briquettes, and pucks, typically granules are regarded as being particles ranging in size from about 80 to about 3 U.S. standard mesh size. Tablets typically fall in the range of from about 0.5 to about 1.0 inch in diameter and about 0.5 to about 1.0 inch in thickness. Briquettes will normally range in size from about 0.5 to about 4.0 inches in length, from about 0.5 to about 4.0 inches in width, and from about 0.5 to about 2.5 inches in thickness. Pucks are normally disc-shaped objects having a diameter up to about 3.0 inches and a thickness in the range of about 0.5 to about 1.0 inch. It will be understood and appreciated however, that these dimensions are not intended to unduly limit the scope of this invention.

If desired, the 1,3-dibromo-5,5-dimethylhydantoin particulate solids of this invention can be formulated with suitable excipients such as binders, lubricants, disintegrants, and mold release agents. Other optional ingredients which may be used in the formulation of products from the 1,3-dibromo-5,5-dimethylhydantoin particulate solids of this invention include fragrances, stabilizers, corrosion inhibitors, dyes, other biocidal agents, surfactants, effervescents, diluents, builders, chelating agents, and the like. Such ancillary materials should of course be compatible with 1,3-dibromo-5,5-dimethylhydantoin and not interfere in any material way with the excellent performance characteristics of the 1,3-dibromo-5,5-dimethylhydantoin particulate solids of this invention. The amount(s) of such ancillary materials used should of course be sufficient to serve the purpose for which it is, or they are, being used. At the same time, the amount used should not materially detract from the physical, mechanical, or performance properties of the formulated product.

As indicated above, the 1,3-dibromo-5,5-dimethylhydantoin particulate solids of this invention can be compacted with or without use of a binder. In the practice of this invention it is preferred to conduct the compaction in the absence of a binder. Commonly-owned co-pending application Ser. No. 09/487,816, filed Jan. 18, 2000, relates in part to the compaction of 1,3-dihalo-5,5-dimethylhydantoins using novel binders described therein.

The following Examples are presented to illustrate the practice of, and advantages made possible by, this invention. These Examples are not intended to limit, and should not be construed as limiting, the scope of this invention to the particular operations or conditions described therein. Examples 1-8 illustrate how the larger average particle sized 1,3-dibromo-5,5-dimethylhydantoin particulate solids of this invention can be prepared. In Examples 1–8, pH was monitored by use of a pH meter, and bromine was fed using a Cole-Parmer Masterflex computerized drive and Easy-Load® pump head. When the continuous operations of Examples 6 and 7 were conducted, the resulting reaction slurry was collected manually and intermittently from the bottom of the reactor. Each fraction was collected in a 500 mL flask.

All particle size determinations referred to in the following Examples were determined by use of a Coulter® LS Particle Size Analyzer. The analyzer was equipped with an LS 230 small volume module and a Fraunhofer PIDS (Polarization Intensity Differential Scattering) detector switched to the "On" position. The determinations are performed at room temperature with a run time of 1 minute per sample. Prior to conducting the particle size determination, and whenever the sample appears to contain particles adhering to each other, the sample is subjected for 15±1 seconds to sonication using a Sonicor Model SC-100T apparatus to ensure that the particle size measurements are on individual particles of the product, rather than temporarily agglomerated particles. Although particle size determinations can be conducted using any procedure and particle size analysis equipment that give accurate particle size measurements of the 1,3-dibromo-5,5-dimethylhydantoin particulate solids, if there is any significant discrepancy in results from one procedure to another and/or in results using one particle size analysis equipment versus another, the procedure and particle size analysis equipment described in this paragraph should be used as described.

EXAMPLE 1

44 Grams of NaOH (1.1 mol) are dissolved in 338 g of water, and 70.4 g of 5,5-dimethylhydantoin (0.55 mol) is added to the NaOH solution. There are 172.0 g of $Br_2$ (1.07 mol) in the bromine reservoir. The reaction flask into which the $Br_2$ and the 5,5-dimethylhydantoin/NaOH solution are fed is maintained at 67° C. with a heating bath. The reaction flask is charged with ~200 mL heel (238 g) of a 1,3-dibromo-5,5-dimethylhydantoin filtrate. The 5,5-dimethylhydantoin/NaOH solution is co-fed to the reaction flask simultaneously with, but separately from, $Br_2$. The bromine is diluted with nitrogen and fed below the surface of the solution in the reaction flask. The reaction mixture is stirred with a mechanical stirrer at a rate of 400 rpm; the pH ranged from 6.7 to 7.1 during the reaction. During the 0.5 hour addition time, the reaction temperature stabilized at 67° C. When the addition of reagents is finished, the orange slurry is discharged from the reaction flask into a beaker and allowed to cool slowly. The slurry is filtered at 45° C. and washed with two 500 mL portions of water. The resultant white solid is dried overnight under a stream of nitrogen. The isolated yield of 1,3-dibromo-5,5-dimethylhydantoin is 130.5 g, a yield of 83% based on 5,5-dimethylhydantoin, or a yield of 85% based on $Br_2$. The active bromine content of the 1,3-dibromo-5,5-dimethylhydantoin is 55.9 wt % (100% of the theoretical value), as determined by iodometric titration. Particle size data on the 1,3-dibromo-5,5-dimethylhydantoin product formed in this operation based on a representative dried sample of the product are summarized in Table 1.

TABLE 1

| Particle Size Category | Particle Size of Product |
| --- | --- |
| Average | 237.5µ |
| 10% is greater than | 371.6µ |
| 25% is greater than | 309.8µ |
| 50% is greater than | 239.1µ |
| 75% is greater than | 165.6µ |
| 90% is greater than | 99.81µ |
| Range | 0.040–541.9µ |

EXAMPLE 2

89 Grams of NaOH (2.2 mol) are dissolved in 676 g of water, and 141 g of 5,5-dimethylhydantoin (1.1 mol) is added to the NaOH solution. There are 350 g of $Br_2$ (2.2 mol) in the bromine reservoir. The reaction flask into which the $Br_2$ and the 5,5-dimethylhydantoin/NaOH solution are fed is maintained at 67° C. with a heating bath. The reaction flask is charged with ~400 mL heel (483 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.1. The reaction temperature stabilized at 67° C. during the 66 minute addition time. When the addition of reagents is finished, the orange slurry is filtered at 43° C. and washed with 1000 mL (2×500 mL) f water. The resultant white solid is dried overnight under a stream of nitrogen. 307.3 Grams of $Br_2$ (1.92 mol) had been fed to the reaction flask. The isolated yield of 1,3-dibromo-5,5-dimethylhydantoin is 212.5 g, a yield of 77% based on $Br_2$, and 68% based on 5,5-dimethylhydantoin; the active bromine content of the 1,3-dibromo-5,5-dimethyl-hydantoin is 55.9 wt % (100% of the theoretical value), as determined by iodometric titration.

EXAMPLE 3

88 Grams of NaOH (2.2 mol) are dissolved in 338 g of water, and 140.8 g of 5,5-dimethylhydantoin (1.1 mol) is added to the NaOH solution. There are 352 g of $Br_2$ (2.2 mol) in the bromine reservoir. The reaction flask into which the $Br_2$ and the 5,5-dimethylhydantoin/NaOH solution are fed is maintained at 69° C. with a heating bath. The reaction flask is charged with ~200 mL heel (240 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.0. The reaction temperature stabilized at 68–69° C. during the 39 minute addition time. When the addition of reagents is finished, the orange slurry is filtered at 40° C. and washed with 500 mL of water. The resultant white solid is dried overnight under a stream of nitrogen. 285.5 Grams of $Br_2$ (1.78 mol) had been fed to the reaction flask. The isolated yield of 1,3-dibromo-5,5-dimethylhydantoin is 186.8 g, a yield of 73% based on $Br_2$, and 60% based on 5,5-dimethylhydantoin; the active bromine content of the 1,3-dibromo-5,5-dimethylhydantoin is 53.4 wt % (96% of the theoretical value), as determined by iodometric titration.

Table 2 summarizes the particle size data for the products of Examples 2 and 3.

TABLE 2

| Particle Size Category | Particle Size of Product - Example 2 | Particle Size of Product - Example 3 |
|---|---|---|
| Average | 210.4μ | 293.6μ |
| 10% is greater than | 381.7μ | 451.2μ |
| 25% is greater than | 298.3μ | 349.6μ |
| 50% is greater than | 196.8μ | 256.3μ |
| 75% is greater than | 115.3μ | 174.9μ |
| 90% is greater than | 56.86μ | 110.6μ |
| Range | 0.040–594.9μ | 0.040–>2000μ |

EXAMPLE 4

44.2 Grams of NaOH (1.1 mol) are dissolved in 338 g of water, and 70.4 g of 5,5-dimethylhydantoin (0.55 mol) is added to the NaOH solution. There are 173 g of $Br_2$ (1.08 mol) in the bromine reservoir. The reaction flask into which the $Br_2$ and the 5,5-dimethylhydantoin/NaOH solution are fed is maintained at 57° C. with a heating bath. The reaction flask is charged with 200 mL heel (244 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 57° C. during the 33 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 139.8 g, a yield of 91% based on $Br_2$, and 89% based on 5,5-dimethylhydantoin; the active bromine content of the 1,3-dibromo-5,5-dimethylhydantoin is 55.7 wt % (99.7% of the theoretical value), as determined by iodometric titration.

EXAMPLE 5

44.2 Grams of NaOH (1.1 mol) are dissolved in 338 g of water, and 70.3 g of 5,5-dimethylhydantoin (0.55 mol) is added to the NaOH solution. There are 172.5 g of $Br_2$ (1.08 mol) in the bromine reservoir. The reaction flask into which the $Br_2$ and the 5,5-dimethylhydantoin/NaOH solution are fed is maintained at 48° C. with a heating bath. The reaction flask is charged with 200 mL heel of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 48° C. during the 34 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 144.8 g, a yield of 94% based on $Br_2$, and 92% based on 5,5-dimethylhydantoin; the active bromine content of the 1,3-dibromo-5,5-dimethylhydantoin is 55.0 wt % (98.4% of the theoretical value), as determined by iodometric titration.

The particle size data for the products of Examples 4 and 5 are summarized in Table 3.

TABLE 3

| Particle Size Category | Particle Size of Product - Example 4 | Particle Size of Product - Example 5 |
|---|---|---|
| Average | 231.2μ | 178.4μ |
| 10% is greater than | 338.3μ | 281.1μ |
| 25% is greater than | 285.0μ | 230.9μ |
| 50% is greater than | 228.8μ | 175.7μ |
| 75% is greater than | 177.8μ | 125.0μ |
| 90% is greater than | 133.0μ | 79.14μ |
| Range | 0.040–493.6μ | 0.040–409.6μ |

EXAMPLE 6

The process of this Example was conducted in a continuous fashion. A feed solution of 5,5-dimethylhydantoin/NaOH was formed by adding 5,5-dimethylhydantoin to a 9 wt % NaOH solution, such that the 5,5-dimethylhydantoin concentration was about 1.1 M. The 5,5-5 dimethylhydantoin/NaOH solution was co-fed to the reaction flask simultaneously with, but separately from, $Br_2$. The flask was suspended in a heating bath. The reaction mixture was stirred with a mechanical stirrer at a rate of 500 rpm. The reaction mixture was maintained at a pH of about 7.0±0.2, and the reaction temperature was maintained at 55° C. Ten fractions of product were collected in an average time of 30 minutes per fraction. The isolated yield of the 1,3-dibromo-5,5-dimethylhydantoin was 90% based on 5,5-dimethylhydantoin, and 92% based on added $Br_2$. The purity of the 1,3-dibromo-5,5-dimethylhydantoin, a white crystalline product, was 99.8%, based on the theoretical bromine content. Fractions 5–10 represent the particle size of the product as formed during steady-state operating conditions. Table 4 summarizes average particle size data and particle size distribution data relating to fractions 5–10 based on samples of each such fraction taken during the steady-state operation of the continuous process. The determinations showed that a bimodal distribution of the product had been produced. The overall average particle size of the product was 512.3 microns.

TABLE 4

| Particle Size | Fraction 5 | Fraction 6 | Fraction 7 | Fraction 8 | Fractions 9 + 10 |
|---|---|---|---|---|---|
| Average | 371.7μ | 445.6μ | 535.5μ | 560.3μ | 549.9μ |
| 10% is greater than | 530.7μ | 626.0μ | 724.7μ | 805.0μ | 952.1μ |
| 25% is greater than | 462.2μ | 550.9μ | 643.3μ | 729.3μ | 833.4μ |

TABLE 4-continued

| Particle Size | Fraction 5 | Fraction 6 | Fraction 7 | Fraction 8 | Fractions 9 + 10 |
|---|---|---|---|---|---|
| 50% is greater than | 386.0μ | 474.5μ | 559.7μ | 641.8μ | 676.7μ |
| 75% is greater than | 256.8μ | 369.6μ | 447.8μ | 436.1μ | 149.6μ |
| 90% is greater than | 94.76μ | 134.4μ | 150.3μ | 94.5μ | 76.02μ |
| Range | 0.791–786.9μ; 1255–1512μ | 4.241–786.9μ; 1143–1255μ | 3.519–863.9μ; 1143–1512μ | 3.519–8.639μ; 1143–1512μ | 0.721–409.6μ; 493.6–1255μ |

EXAMPLE 7

Another continuous operation was conducted in a manner similar to that of Example 6. The feed solution was formed by dissolving 355 g (8.87 mols) in 3550 g of water. To this was added 560 g (4.37 mols) of 5,5-dimethylhydantoin. The concurrent feeds were adjusted to maintain the pH of the aqueous reaction mixture at 7.0±0.2. The temperature was maintained at 55° C. The total amount of bromine ($Br_2$) fed was 1359.4 g (8.50 mols). As in Example 6, ten fractions of the reaction mixture were collected. However, in this operation, the addition rates were adjusted such that the average residence time was approximately 1 hour per fraction. The total isolated yield of 1,3-dibromo-5,5-dimethylhydantoin was 88% based on 5,5-dimethylhydantoin used and 90% based on the added bromine. The 1,3-dibromo-5,5-dimethylhydantoin product was obtained as a white crystalline solid. Table 5 summarizes the average particle size data and product distribution data relating to the product formed in this reaction. Fractions 5–10 represent the particle size of the product as formed during steady-state operating conditions. As in Example 6, the product formed was bimodal. In Table 5 "n.d." indicates that the particle size determination for the larger particle sized fraction was not determined; the instrument used could not measure particles having a particle size greater than 2000 microns. The overall average particle size of the product was at least 455.5 microns.

TABLE 5

| Particle Size | Fraction 5 | Fraction 6 | Fraction 7 | Fraction 8 | Fractions 9 + 10 |
|---|---|---|---|---|---|
| Average | 421.2μ | 478.6μ | 494.0μ | 536.6μ | 631.9μ |
| 10% is greater than | 606.5μ | 699.1μ | 781.7μ | 1063μ | 1438μ |
| 25% is greater than | 532.1μ | 623.4μ | 681.5μ | 813.9μ | 995.7μ |
| 50% is greater than | 452.3μ | 535.0μ | 548.5μ | 546.7μ | 522.8 |
| 75% is greater than | 340.0μ | 372.2μ | 176.6μ | 150.3μ | 160.7μ |
| 90% is greater than | 140.8μ | 112.8μ | 68.94μ | 72.93 | 81.68μ |
| Range | 2.423–786.9μ; n.d. | 2.423–863.9μ; n.d. | 1.520–863.9μ; 1255–1512μ | 0.04–2000μ; n.d. | 0.04–>2000μ; n.d. |

EXAMPLE 8

Another continuous operation was performed using a glass reactor into which were concurrently fed, on a continuous basis, an aqueous solution formed from 5,5-dimethylhydantoin and NaOH, and a separate feed of bromine. The aqueous solution was made by adding 5,5-dimethylhydantoin to an aqueous 9 wt % NaOH solution. This solution contained about 22.4 wt % of 5,5-dimethylhydantoin and 7 wt % NaOH. A one liter,jacketed reactor having an interior diameter of 82 millimeters equipped with an anchor agitator, with an outer diameter of 72 millimeters, was used, and a silicone fluid (Rhodersil 4720V20 fluid; Rhone-Poulenc) was circulated through the jacketing. The temperature of the reaction was controlled at 38° C. Both feeds were controlled by pumps; the average feed rate of the 5,5-dimethylhydantoin/NaOH solution was 15.84 grams/minute via a Prominent Gamma G/4A positive displacement pump, and the average feed rate of the bromine was 4.67 grams/minute via a Masterflex Easy-Load peristaltic pump. The reaction mixture was stirred at 400 rpm. The pH of the reaction was monitored by measuring the pH of the effluent using a pH meter, and the pH ranged from 6.06 to 6.36 during the reaction. Product removal from the reactor was also controlled by a pump. Residence time was, on average, 30 minutes per fraction; each fraction was about 500 mL. A yield of 90.5% of 1,3-dibromo-5,5-dimethylhydantoin was obtained, based on the amount of 5,5-dimethylhydantoin fed to the reactor. The active bromine content of the 1,3-dibromo-5,5-dimethylhydantoin was >55.3%, as determined by standard iodometric titration. Thus, the purity of this product was greater than 99.0%.

Table 6 summarizes particle size data on the 1,3-dibromo-5,5-dimethylhydantoin product formed in the continuous operation of Example 8. These data are averaged data based on two samples taken at different times during the continuous operation once steady state conditions, or essentially steady state conditions, had been achieved.

TABLE 6

| Particle Size Category | Particle Size of Product |
|---|---|
| Average | 188.9μ |
| 10% is greater than | 295.2μ |
| 25% is greater than | 255.6μ |
| 50% is greater than | 203.1μ |
| 75% is greater than | 122.5μ |
| 90% is greater than | 55.9μ |
| Range | 0.872–356.5μ |

EXAMPLE 9

Samples of commercially-available N,N'-dihalo-5,5-dimethylhydantoins were obtained and subjected to standard test procedures in order to determine their average particle size using the Coulter® LS Particle Size Analyzer. Table 7 summarizes the results of these average particle size determinations, and also sets forth the data obtained in the same way on a representative sample of the 1,3-dibromo-5,5-dimethylhydantoin product of this invention produced in Example 6. Table 8 summarizes the particle size distribution data on the commercially-available 1,3-dihalo-5,5-dimethylhydantoins. In Table 8 the following abbreviations are used: DCDMH is 1,3-dichloro-5,5-dimethylhydantoin; BCDMH is N,N'-bromochloro-5,5-dimethylhydantoin; and DBDMH is 1,3-dibromo-5,5-dimethylhydantoin.

TABLE 7

| N,N'-dihalo-5,5-dimethylhydantoin | Source | Average Particle Size |
|---|---|---|
| 1,3-dichloro-5,5-dimethylhydantoin | Aldrich Chemical Co. | 108.1 microns |
| N,N'-bromochloro-5,5-dimethylhydantoin | Aldrich Chemical Co. | 323.8 microns |
| 1,3-dibromo-5,5-dimethylhydantoin | Aldrich Chemical Co. | 162.1 microns |
| 1,3-dibromo-5,5-dimethylhydantoin | Albemarle Corporation | 64.5 microns |
| 1,3-dibromo-5,5-dimethylhydantoin | Great Lakes Chemical Corporation | 45.2 microns |
| 1,3-dibromo-5,5-dimethylhydantoin | The present invention | 293.6 microns |

TABLE 8

| Particle Size | DCDMH - Aldrich | BCDMH - Aldrich | DBDMH - Aldrich | DBDMH - Albemarle | DBDMH - Great Lakes |
|---|---|---|---|---|---|
| Average | 108.1µ | 323.8µ | 162.1µ | 64.59µ | 45.23µ |
| 10% is greater than | 195.3µ | 877.9µ | 359.2µ | 162.7µ | 78.76µ |
| 25% is greater than | 134.4µ | 409.9µ | 177.6µ | 90.12µ | 49.76µ |
| 50% is greater than | 80.07µ | 173.9µ | 86.03µ | 39.21µ | 34.68µ |
| 75% is greater than | 45.99µ | 65.39µ | 47.37µ | 26.85µ | 23.25µ |
| 90% is greater than | 27.19µ | 29.35µ | 27.67µ | 17.91µ | 13.90µ |
| Range | 0.04–>2000µ | 0.04–>2000µ | 0.04–>2000µ | 0.04–309.6µ | 0.04–409.6µ |

EXAMPLE 10

The color characteristics of samples of the bromine-containing N,N'-dihalo-5,5-dimethylhydantoins referred to in Example 9 were determined using Hunter Lab Color Quest Model 450 instrument. The test determined the Yellowness Index of the powder using the foregoing instrument which is approved for use in accordance with ASTM test designation E 313-96 "Standard Practice for Calculating Yellowness and Whiteness Indices from Instrumentally Measured Color Coordinates". The instrument includes a station for receiving a crucible filled with the powder to be tested for its color characteristics, and a pair of light sources disposed above the crucible. A first such light source is spaced and positioned directly above the surface of the crucible and its contents so as to direct a beam of light at a 90° angle relative to the horizontal upper surface of the contents of the crucible. The second such light source is spaced and positioned so as to direct a beam of light at a 45° angle relative to the horizontal upper surface of the contents of the crucible. One photomultiplier detector is positioned directly above the first such light source so as to receive the reflected light from the surface receiving the beam of light from the first light source. Another photomultiplier detector is positioned at a 90° angle relative to the beam of light issuing from the second light source so as to receive the reflected light from the surface receiving the beam of light from the second light source. Each such photomultiplier measures the wavelength and the amount of the reflected beam and inputs such data to a microprocessor programmed to calculate from such data a value for the Yellowness Index of the powder. The results of these evaluations in terms of Yellowness Index (YI) are summarized in Table 9. The higher the numerical value of the Yellowness Index, the more yellow the product.

TABLE 9

| N,N'-dihalo-5,5-dimethylhydantoin | Source | Yellowness Index |
|---|---|---|
| N,N'-bromochloro-5,5-dimethylhydantoin | Aldrich Chemical Co. | 12.82 |
| 1,3-dibromo-5,5-dimethylhydantoin | Aldrich Chemical Co. | 37.82 |
| 1,3-dibromo-5,5-dimethylhydantoin | Albemarle Corporation | 31.22 |
| 1,3-dibromo-5,5-dimethylhydantoin | Great Lakes Chemical Corporation | 21.28 |
| 1,3-dibromo-5,5-dimethylhydantoin | The present invention | 11.65 |

EXAMPLE 11

Five-gram samples of 1,3-dibromo-5,5-dimethylhydantoin of this invention were compacted without binder in a Sintech(V press (MTS Systems Corporation, Edenprairie, Minn.) equipped with a punch and die fabricated from Hastelloy® C alloy. Before manually filling the die, the interior surfaces of the die where lightly dusted with a micronized polypropylene wax (MICROPRO 400 wax; Micro Powders, Incorporated, Tarrytown, N.Y.). The pressure applied was 5000 psi with no dwell time, i.e., the pressure was automatically terminated immediately reaching 5000 psi. The resultant tablets after removal from the die were aged for 6 days at room temperature. Thereupon the tablets were subjected to crush strength testing utilizing a Sintech® 1/S compression apparatus (MTS Systems Corporation, Edenprairie, Minn.) equipped with Testworks software, which software is installed in the I/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the tablet with the micrometer to provide a digitized input to the computer. Next the tablet is placed on its edge on the load cell with the piston in contact with the upper edge of the tablet. Then the apparatus is activated whereby the piston commences applying a progressively increasing downward diametral force to the tablet. At the same time, the load cell continuously measures the downward force being applied to the tablet, and the input of such measurements is transmitted to the computer. When the force being applied reaches the point where the amount of force suddenly decreases to 10% of the immediately preceding force, the tablet has reached the breaking point, and the application of the force is immediately terminated by the software program. From the inputs to the computer, two values are provided, namely the pounds of force at the breaking point of the tablet, and the pounds of force per inch thickness of the tablet at the breaking point. Thus the greater the force applied, the greater the crush strength. Two groups of such tests were conducted. One set (Set A) involved forming and evaluating 5 tablets from a batch of 1,3-dibromo-5,5-dimethylhydantoin of this invention produced in a continuous process of the type described in Example 8. The other set (Set B) of tests involved 3 tablets produced from the 1,3-dibromo-5,5-dimethylhydantoin produced in the batch process of Example 2, a product having an average particle size of about 210 microns. Table 10 summarizes the results of these tests.

TABLE 10

| Test Set | Tablet Thickness | Crush Strength | Crush Strength |
|---|---|---|---|
| A | 0.365 in. | 20.9 lb. | 57.3 lb./in. |
| A | 0.367 in. | 25.5 lb. | 69.5 lb./in. |
| A | 0.366 in. | 19.2 lb. | 52.5 lb./in. |
| A | 0.367 in. | 22.8 lb. | 62.1 lb./in. |
| A | 0.364 in. | 23.7 lb. | 65.0 lb./in. |
| Avg. of A | — | 22.4 lb. | 61.3 lb./in. |
| B | 0.353 in. | 10.7 lb. | 30.4 lb./in. |
| B | 0.352 in. | 12.8 lb. | 36.4 lb./in. |
| B | 0.354 in. | 9.8 lb. | 27.8 lb./in. |
| Avg. of B | — | 11.1 lb. | 31.5 lb./in. |

As noted above, tablets of conventional 1,3-dibromo-5,5-dimethylhydantoin devoid of binder cannot be tableted in the manner described above.

EXAMPLE 12

The crush strength of tablets formed from 1,3-dibromo-5,5-dimethylhydantoin of this invention formulated with a binder was illustrated in a group of tests conducted as described in Example 11. The procedure for producing the tablets was as follows: 1,3-dibromo-5,5-dimethylhydantoin produced in Example 8 was hand-mixed with 3% by weight of micronized polyethylene wax from Micro Powders Incorporated, Tarrytown, N.Y. for approximately 30 minutes. The resultant formulation was then converted into tablets as described in Example 11. The results of the crush strength tests, conducted as described in Example 11, are summarized in Table 11.

TABLE 11

| Tablet Thickness | Crush Strength | Crush Strength |
|---|---|---|
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

EXAMPLE 13

Comparative flowability tests were carried out using a sample of 1,3-dibromo-5,5-dimethylhydantoin of this invention and samples of the commercially-available products referred to in Example 9. These tests involved filling an 8-ounce glass jar to about one-third of its capacity with the sample to be tested. After closing the jar, it was slowly rotated while on its side in a single direction while observing the characteristics of the contents. Table 12 summarizes the observations made in these flowability tests.

TABLE 12

| N,N'-dihalo-5,5-dimethylhydantoin | Source | Product Characteristics |
|---|---|---|
| 1,3-dichloro-5,5-dimethylhydantoin | Aldrich Chemical Co. | Bridging occurred; high dusting, non-free-flowing powder |
| N,N'-bromochloro-5,5-dimethylhydantoin | Aldrich Chemical Co. | Bridging occurred; high dusting, non-free-flowing powder |
| 1,3-dibromo-5,5-dimethylhydantoin | Aldrich Chemical Co. | Bridging occurred; high dusting, non-free-flowing powder |
| 1,3-dibromo-5,5-dimethylhydantoin | Albemarle Corporation | Bridging occurred; high dusting, non-free-flowing powder |
| 1,3-dibromo-5,5-dimethylhydantoin | Great Lakes Chemical Corporation | Bridging occurred; high dusting, non-free-flowing powder |
| 1,3-dibromo-5,5-dimethylhydantoin | The present invention | No bridging occurred; low dusting, free-flowing powder |

EXAMPLE 14

The commercially-available 1,3-dihalo-5,5-dimethylhydantoins referred to in Example 9 were subjected to tableting operations as described in Example 11, except that the tests on DCDMH and BCDMH from Aldrich involved 4 gram samples, and the tableting and crush strength tests as described in Example 11 were conducted using three samples each. It was found that three such materials, all of which were 1,3-dibromo-5,5-dimethyhydantoin products obtained from three separate commercial sources, could not be tableted. The results of these operations are summarized in Table 13. Each of the crush strength values shown is the average of three tests.

TABLE 13

| Particle Size | DCDMH - Aldrich | BCDMH - Aldrich | DBDMH - Aldrich | DBDMH - Albemarle | DBDMH - Great Lakes |
|---|---|---|---|---|---|
| Average | 108.1μ | 323.8μ | 162.1μ | 64.59μ | 45.23μ |
| 10% is greater than | 195.3μ | 877.9μ | 359.2μ | 162.7μ | 78.76μ |
| 25% is greater than | 134.4μ | 409.9μ | 177.6μ | 90.12μ | 49.76μ |
| 50% is greater than | 80.07μ | 173.9μ | 86.03μ | 39.21μ | 34.68μ |
| 75% is greater than | 45.99μ | 65.39μ | 47.37μ | 26.85μ | 23.25μ |
| 90% is greater than | 27.19μ | 29.35μ | 27.67μ | 17.91μ | 13.90μ |
| Range | 0.04–>2000μ | 0.04–>2000μ | 0.04–>2000μ | 0.04–309.6μ | 0.04–409.6μ |
| Compaction | Intact tablets | Intact tablets | Delaminated; broken tablets | Delaminated; broken tablets | Delaminated; broken tablets |
| Crush strength lb/in | 183.6 | 83.9 | Test not possible | Test not possible | Test not possible |

The process for producing the novel 1,3-dibromo-5,5-dimethylhydantoin particulate solids of this invention as described in commonly-owned co-pending application Ser. No. 09/484,844, filed Jan. 18, 2000, comprises, for example, concurrently feeding (i) an aqueous solution or slurry formed from an inorganic base and 5,5-dimethylhydantoin, and (ii) a brominating agent in proportions such that each nitrogen atom is substituted by a bromine atom, thereby continuously forming product which precipitates in an aqueous reaction mixture. The pH of the mixture is continuously maintained in the range of about 5.5 to about 8.5.

As used herein, including the claims, the term "pressure-compactible" means that the substance in particulate form, and without prior treatment to enhance its compactibility, can be converted into a shape-retentive tablet when subjected to the following conditions:
1) A 0.71 inch diameter circular die fabricated from Hastelloy C alloy is lightly dusted with micronized polypropylene wax (MICROPRO 400 wax; Micro Powders, Incorporated, Tarrytown N.Y., or equivalent if MICROPRO 400 wax is not available).
2) A representative five-gram sample of the given 1,3-dibromo-5,5-dimethylhydantoin is manually placed into the above die.
3) The five-gram sample is pressure compacted in the die at 5000 psi using a Sintech® press (MTS Systems Corporation, Edenprairie, Minn.) equipped with a punch fabricated from Hastelloy® C alloy to form a 0.71-inch diameter circular tablet. No dwell time is used, i.e., the pressure is released just as soon as the pressure reaches 5000 psi.
4) If no appreciable delamination or breakage occurs when the tablet is released from the die, the given 1,3-dibromo-5,5-dimethylhydantoin is deemed "pressure-compactible".

Conversely, the term "non-compactible" means that the 1,3-dibromo-5,5-dimethylhydantoin particulate solids referred to cannot be successfully converted into a shape-retentive tablet under the conditions just described in the immediately preceding paragraph.

As used herein, including the claims, values given for crush strength are as measured using the apparatus and procedure as described in Example 11 above. When the compacted article is in a form other than a cylindrical tablet (e.g., a granule, caplet, or briquette), the article being tested is to be positioned on the load cell and under the screw-driven piston with the longest axis of the article in the vertical position. In addition, the micrometer is used to measure the thickest portion of the article when the article is positioned on the load cell and under the screw-driven piston with the longest axis of the article in the vertical position.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions specified in this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. As a composition of matter, 1, 3-dibromo- 5,5-dimethylhydantoin particulate solids characterized by having:
   A) an average particle size of at least about 175 microns but less than 300 microns, with 50% by weight of the particles having a particle size of at least about 180 microns, or
   B) an average particle size in the range of 300 to about 700 microns, with 50% by weight of the particles having a particle size of at least about 350 microns.

2. A composition of claim 1 wherein said average particle size is at least about 300 microns.

3. A composition of claim 1 wherein said average particle size is at least about 400 microns.

4. A composition of claim 1 wherein said average particle size is at least about 500 microns.

5. A composition of claim 1 wherein said 1,3-dibromo-5,5-dimethylhydantoin particulate solids have an average particle size of at least about 175 microns but less than 300 microns, and wherein 10 percent by weight of the particles have a particle size of at least about 280 microns, 25 percent by weight of the particles have a particle size of at least about 240 microns, 50 percent by weight of the particles have a particle size of at least about 180 microns, 75 percent by weight of the particles have a particle size of at least about 100 microns, and 90 percent by weight of the particles have a particle size of at least about 45 microns.

6. A composition of claim 1 wherein said 1,3-dibromo-5,5-dimethylhydantoin particulate solids have an average particle size in the range of 300 to about 700 microns, and wherein 10 percent by weight of the particles have a particle size of at least about 500 microns, 25 percent by weight of the particles have a particle size of at least about 440 microns, 50 percent by weight of the particles have a particle size of at least about 350 microns, 75 percent by weight of the particles have a particle size of at least about 120 microns, and 90 percent by weight of the particles have a particle size of at least about 50 microns.

7. A composition of any of claims 1, 2, 3, 4, 5, or 6 herein said particulate solids, in the absence of a binder and without any prior treatment to impart compactability to the solids, are pressure compactable into a tablet which can be extracted from the die without breaking.

8. A composition of any of claims 1, 2, 3, 4, 5, or 6 wherein said particulate solids have a Yellowness Index of no greater than about 15.

9. A composition of any of claims 1, 2, 3, 4, 5, or 6 wherein said particulate solids, in the absence of a binder and without any prior treatment to impart compactability to the solids, are pressure compactable into a tablet which can be extracted from the die without breaking, and wherein said particulate solids have a Yellowness Index of no greater than about 15.

10. Pressure-compactible 1,3-dibromo-5,5-dimethylhydantoin particulate solids devoid of treatment to impart compactibility to said solids, and having:
   A) an average particle size of at least about 175 microns but less than 300 microns, with 50% by weight of the particles having a particle size of at least about 180 microns, or
   B) an average particle size in the range of 300 to about 700 microns, with 50% by weight of the particles having a particle size of at least about 350 microns;

said solids being further characterized in that when a five-gram sample of said solids is manually packed into a die of Hastelloy C alloy lightly dusted with micronized polypropylene wax and pressure compacted at 5000 psi into a 0.71-inch diameter tablet, said tablet, after aging at room temperature for 6 days, has a crush strength in the diametral direction of at least 25 pounds per inch of thickness.

11. An article which comprises a binder-free compacted form of 1,3-dibromo-5,5-dimethylhydantoin having, prior to compaction:
A) an average particle size of at least about 175 microns but less than 300 microns, with 50% by weight of the particles having a particle size of at least about 180 microns, or
B) an average particle size in the range of 300 to about 700 microns, with 50% by weight of the particles having a particle size of at least about 350 microns.

12. An article according to claim 11 wherein said article is in the form of granules.

13. An article according to claim 11 wherein said article is in the form of a tablet.

14. An article according to claim 11 wherein said article is in the form of a briquette.

15. An article according to claim 11 wherein said article is in the form of a tablet or a briquette having a crush strength of at least about 25 pounds per inch of thickness.

16. A method of producing a compacted article from 1,3-dibromo-5,5-dimethylhydantoin, said method comprising pressure compacting in the absence of a binder, pressure compactable 1,3-dibromo-5,5-dimethylhydantoin particulate solids devoid of prior treatment to impart compactability to said solids, said 1,3-dibromo-5,5-dimethylhydantoin particulate solids having, prior to being compacted:
A) an average particle size of at least about 175 microns but less than 300 microns, with 50% by weight of the particles having a particle size of at least about 180 microns, or
B) an average particle size in the range of 300 to about 700 microns, with 50% by weight of the particles having a particle size of at least about 350 microns.

17. A method according to claim 16 wherein said particulate solids are pressure compacted into tablets which can be extracted from the die without breaking.

18. A method according to claim 16 wherein said particulate solids are pressure compacted into briquettes which can be extracted from the die without breaking.

19. A method according to claim 16 wherein the pressure used to produce said compacted article is in the range of from about 1000 psi to about 30,000 psi.

20. A method according to claim 16 wherein said article is in the form of a tablet having in the diametral direction a crush strength of at least about 25 pounds per inch of thickness.

21. A method according to claim 16 wherein said article is in the form of a briquette having in the longitudinal direction a crush strength of at least about 25 pounds per inch of thickness.

22. An article produced according to the method of claim 16 wherein said article produced has a Yellowness Index of no greater than about 15.

23. An article according to claim 22 wherein said article is in the form of granules, a tablet, or a briquette.

24. An article according to claim 23 wherein said article is in the form of a tablet having in the diametral direction a crush strength of at least about 25 pounds per inch of thickness.

25. An article according to claim 23 Wherein said article is in the form of a briquette having in the longitudinal direction a crush strength of at least about 25 pounds per inch of thickness.

26. A method of improving the removal of 1,3-dibromo-5,5-dimethylhydantoin particulate solids from a hopper or feeder, said method comprising discharging from said hopper or feeder 1,3-dibromo-5,5-dimethylhydantoin particulate solids having:
A) an average particle size of at least about 175 microns but less than 300 microns, with 50% by weight of the particles having a particle size of at least about 180 microns,
B) an average particle size in the range of 300 to about 700 microns, with 50% by weight of the particles having a particle size of at least about 350 microns,
such that the 1,3-dibromo-5,5-dimethylhydantoin being discharged flows freely from said hopper or feeder without bridging or ratholing.

27. A method according to claim 26 wherein said average particle size is at least about 200 microns.

28. A method according to claim 26 wherein said average particle size is at least about 300 microns.

29. A method according to claim 26 wherein said average particle size is at least about 400 microns.

30. A method according to claim 26 wherein said average particle size is at least about 500 microns.

31. A method according to claim 26 wherein said 1,3-dibromo-5,5-dimethylhydantoin particulate solids have an average particle size of at least about 175 microns but less than 300 microns, and wherein 10 percent by weight of the particles have a particle size of at least about 280 microns, 25 percent by weight of the particles have a particle size of at least about 240 microns, 50 percent by weight of the particles have a particle size of at least about 180 microns, 75 percent by weight of the particles have a particle size of at least about 100 microns, and 90 percent by weight of the particles have a particle size of at least about 45 microns.

32. A method according to claim 26 wherein said 1,3-dibromo-5,5-dimethylhydantoin particulate solids have an average particle size in the range of 300 to about 700 microns, and wherein 10 percent by weight of the particles have a particle size of at least about 500 microns, 25 percent by weight of the particles have a particle size of at least about 440 microns, 50 percent by weight of the particles have a particle size of at least about 350 microns, 75 percent by weight of the particles have a particle size of at least about 120 microns, and 90 percent by weight of the particles have a particle size of at least about 50 microns.

* * * * *